US008732918B2

(12) United States Patent
Carter

(10) Patent No.: US 8,732,918 B2
(45) Date of Patent: May 27, 2014

(54) SYSTEM AND METHOD FOR QUICK RELEASE

(76) Inventor: Paul Carter, Fayetteville, NC (US)

( * ) Notice: Subject to any disclaimer, the term of this patent is extended or adjusted under 35 U.S.C. 154(b) by 497 days.

(21) Appl. No.: 12/994,135

(22) PCT Filed: May 22, 2009

(86) PCT No.: PCT/US2009/044950
§ 371 (c)(1),
(2), (4) Date: Jun. 21, 2011

(87) PCT Pub. No.: WO2009/143410
PCT Pub. Date: Nov. 26, 2009

(65) Prior Publication Data
US 2011/0239419 A1 Oct. 6, 2011

Related U.S. Application Data

(60) Provisional application No. 61/055,267, filed on May 22, 2008.

(51) Int. Cl.
A44B 11/00 (2006.01)
A44B 11/25 (2006.01)

(52) U.S. Cl.
USPC ........... 24/634; 24/606; 24/614; 24/615; 24/616

(58) Field of Classification Search
USPC ............... 24/614–616, 625, 606, 634
See application file for complete search history.

(56) References Cited

U.S. PATENT DOCUMENTS 2,986,362 A 5/1961 Gimalouski
6,487,761 B2 12/2002 Van Tassel
6,581,989 B2 * 6/2003 Markisello ............ 292/338.3
7,207,522 B2 * 4/2007 Parrott et al. ............ 244/107
2002/0092140 A1 * 7/2002 Van Tassel ............... 24/614
2005/0115999 A1 6/2005 Johnson (Continued)

FOREIGN PATENT DOCUMENTS

GB 2144511 A * 3/1985 ............ G05G 9/00
JP 06-6999 U 1/1994

(Continued)

OTHER PUBLICATIONS

International Search report issued on Jan. 6, 2010 in the corresponding PCT application No. PCT/US2009/044950.

Primary Examiner — Robert J Sandy
Assistant Examiner — Louis Mercado
(74) Attorney, Agent, or Firm — Michael J. Dimino, Esq.; Johnson, Marcou & Isaacs, LLC

(57) ABSTRACT

The system and method for quick release can include a remote release enclosure having a connection side and a trigger side, at least one cable assembly traversing through the release enclosure from the connection side to the trigger side, a trigger assembly coupled the at least one cable assembly, and a plurality of attachment assemblies coupled the other end of the at least one cable assembly. The trigger assembly can be operatively coupled to each of the plurality of attachment assemblies via the cable assemblies. The attachment assemblies can have a male portion having an inner guide post between at least two outer guide posts and a female portion. The cable assemblies can couple the male portions of the attachment assemblies to the trigger assembly such that movement of the trigger assembly can release or disengage the male portion of the attachment assembly from the female portion.

10 Claims, 4 Drawing Sheets

(56) References Cited

U.S. PATENT DOCUMENTS

| | | | |
|---|---|---|---|
| 2006/0110230 A1* | 5/2006 | Girardin | 410/7 |
| 2008/0178778 A1* | 7/2008 | Koning et al. | 108/132 |
| 2012/0030852 A1* | 2/2012 | Anscher | 2/102 |

FOREIGN PATENT DOCUMENTS

| | | |
|---|---|---|
| JP | 06-311911 A | 11/1994 |
| KR | 20-0189037 Y1 | 7/2000 |
| KR | 10-2004-0079424 A | 9/2004 |

\* cited by examiner

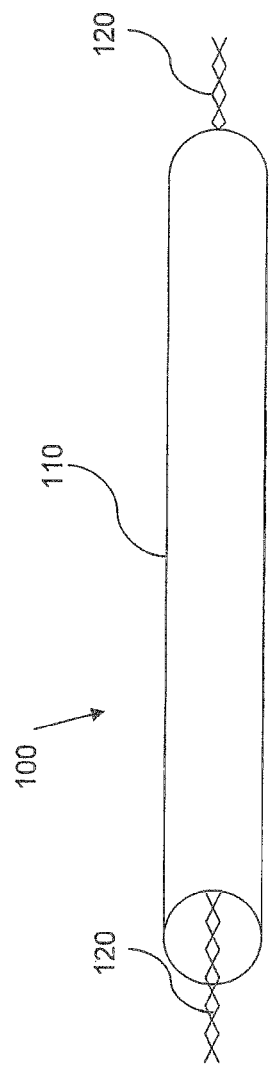

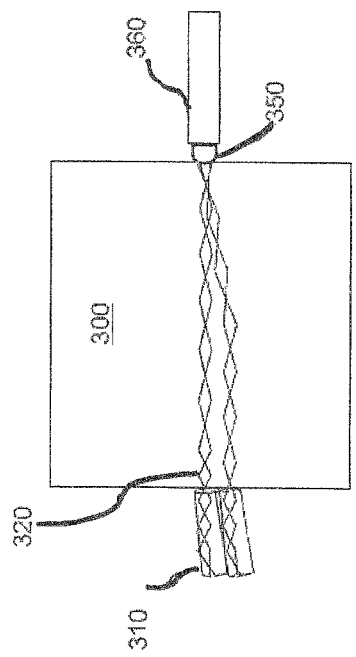
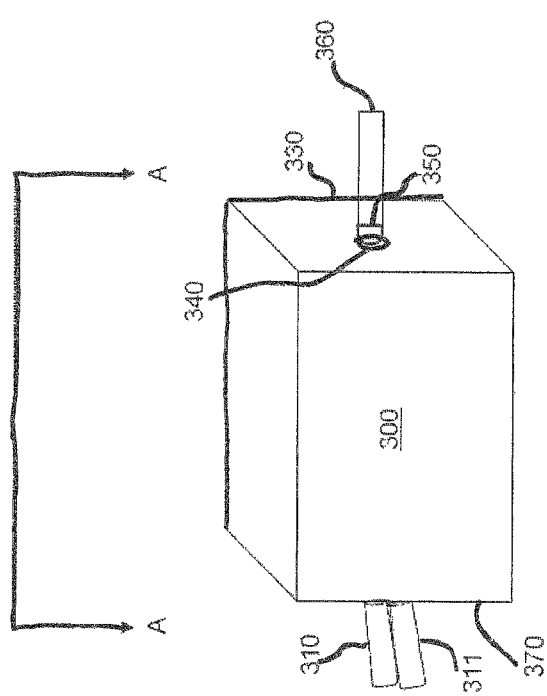

SYSTEM AND METHOD FOR QUICK RELEASE

CROSS-REFERENCE TO RELATED APPLICATIONS

The present disclosure claims priority to and the benefit under 35 U.S.C. §119(e) of U.S. Provisional Application Ser. No. 61/055,267 filed May 22, 2008.

TECHNICAL FIELD

The present technology relates to a remote release assembly for use with one or more attachment assemblies. More particularly, the technology relates to a system and method of detaching one or more attachment assemblies from a single, remotely-located release assembly with trigger.

BACKGROUND OF THE INVENTION

Currently, soldiers are issued large quantities of equipment to increase lethality, survivability, mobility and/or target acquisition capabilities. Often, little consideration is given to item deployment, storage, transport and/or utilization. A soldier can therefore find himself forced to place items in hard-to-reach locations when securing issued equipment to his person. This can lead to inefficiencies in both carrying equipment and accessing equipment for use. Without the ability to quickly detach necessary items from a soldier's person, a soldier's life can be unnecessarily endangered. Moreover, detached items must be easily reattached. A system and method of attaching and quickly detaching multiple pieces of equipment to a soldier is, therefore, required.

SUMMARY OF THE INVENTION

Accordingly, the present technology has been achieved to solve the above problems and carry out a further improvement. The present technology discloses a system and method of attaching and quickly detaching a number of items comprising: a remote release enclosure having a connection side and a trigger side, at least one cable assembly traversing through the release enclosure from the connection side to the trigger side, a trigger assembly coupled the at least one cable assembly, and a plurality of attachment assemblies coupled the other end of the at least one cable assembly.

BRIEF DESCRIPTION OF THE DRAWINGS

FIG. 1 is a perspective view of a cable assembly for the system for quick release in accordance with an exemplary embodiment;

FIG. 3A is a perspective view of a remote trigger assembly for the system for quick release in accordance with an exemplary embodiment;

FIG. 3B is a cross-sectional view along axis A-A of the remote trigger assembly for the system for quick release depicted in FIG. 3A in accordance with an exemplary embodiment.

DETAILED DESCRIPTION

Figure 2B:
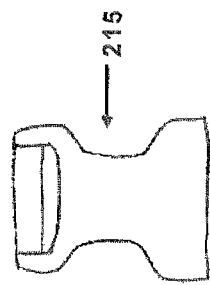
FIG. 2B is a frontal view of a female portion of an attachment assembly for the system for quick release in accordance with an exemplary embodiment.

Reference will now be made in detail to embodiments of the technology. Each example is provided by way of explanation of the technology only, not as a limitation of the technology. It will be apparent to those skilled in the art that various modifications and variations can be made in the present technology without departing from the scope or spirit of the technology. For instance, features described as part of one embodiment can be used on another embodiment to yield a still further embodiment. Thus, it is intended that the present technology cover such modifications and variations that come within the scope of the technology.

As is shown in FIG. 1, an embodiment of the present technology comprises at least one cable assembly 100. The at least one cable assembly can comprise an outer shell 110 and can have a plurality of inner cables 120 or wires running coaxially therewithin. The outer shell 110 can be of any shape known in the art. For example, the outer shell 110 can be cylindrical, triangular, rectangular, or any other similar shape. Alternatively, the outer shell 110 can also be a hollow outer wire. Each of the plurality of inner cables 120 or wires can consist of two or more members. The members can be strands, cables, cords, or wires that are braided, entwined, or wrapped. The outer shell 110 and/or the plurality of inner cables 120 can be made of a flexible material with little stretch. For example, the outer shell 110 and/or inner cables 120 can be made of bungee cord, elastic cord, nylon cord, or any other similar flexible material. With flexible material having little stretch, it is well known that as the diameter of each inner cable 120 increases, the resistance required to tension each inner wire 120 will increase. The length of the cable assembly 100 can vary depending on the required use, and this variance can also affect the resistance required to tension the inner cable 120.

Figure 2A:
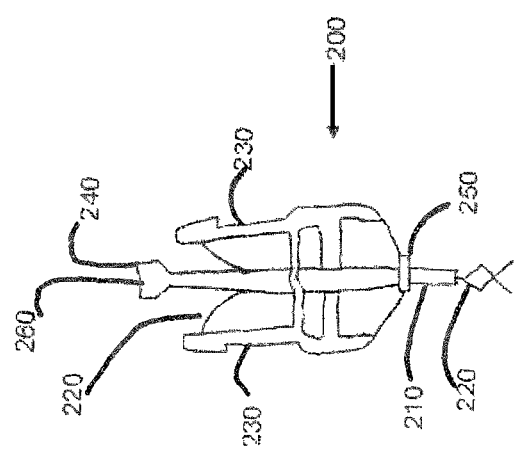
FIG. 2A is a frontal view of a male portion of an attachment assembly for the system for quick release in accordance with an exemplary embodiment.

As is shown in FIGS. 2A and 2B, an exemplary embodiment of the present technology comprises an attachment assembly which can be used for the attachment of utility items to a larger platform. The attachment assembly can comprise a male portion 200 and a female portion 215, both of which can be configured for mating engagement with each other. For example, the male portion 200 and the female portion 215 can be configured such that they can be locked, attached, inserted, buckled or fit together to form a single unit. The attachment assembly can be a side-release buckle, a side buckle, a snap buckle, an end release buckle, or any other similar attachment assembly as is known in the art. Both the male portion 200 and female portion 215 can be made of a number of materials including, but not limited to, metals and plastics depending on the required use. For example, the attachment assembly illustrated in FIGS. 2A and 2B has a male portion having an inner guide post 240 between two outer guide posts 230 and a female portion 215 having apertures for matingly engaging the inner guide post 240 and outer guide posts 230 of the male portion 200. When the female portion 215 and male portion 200 of the attachment assembly shown in FIGS. 2A and 2B engage, the inner guide post 240 and outer guide posts 230 snap, secure, or fasten in place with the apertures of the female portion 215.

The male portion 200 can comprises an inner guide post 240 between at least two outer guide posts 230. The outer shell 210 of the cable assembly (See FIG. 1, 100) can be coupled to the proximal end 250 of the male portion 200 of a corresponding attachment assembly, while at least one of the plurality of inner cables 220 extends transversely through the inner guide post 240 of the corresponding attachment assembly towards the distal end 260 of the male portion 200. Alternatively, the outer shell 210 of the cable assembly can be anchored to the proximal end of the male portion 200 of a corresponding attachment assembly. Each of the plurality of inner cables 220 can have at least two members, such as attachment portions, braided cords, two entwined cords, or any other types of members. As illustrated in FIG. 2A, the two attachment portions of each of the plurality of inner cables 220 can be configured such that one of the attachment portions couples to the outer guide post 230 located to the right side of the inner guide post 240, and a second one of the attachment portions couples to the outer guide post 230 located to the left side of the inner guide post 240. For example, one of the braided cords of one of the plurality of inner cables 220 can extend from the inner guide post 240 and attach to an inner wall of one of the outer guide posts 230. In at least some embodiments, one of the plurality of inner cables 220 extends through the inner guide post 230 of at least one of the respective male portions 200, and at least two of the braids of the one of the plurality of inner cables 220 exit the inner guide post 240 and are coupled to an outer guide post 230 located on opposite sides of the inner guide post 240.

When one of the plurality of inner cables 220 is tensioned, the outer guide posts 230 can move closer to or approach the inner guide post 240 based upon the above couplings of the inner cable 220 to the outer guide posts 230. Consequently, the male portion 200 can be disengaged or unlocked from the female portion 215. In one exemplary embodiment, the outer guide posts 230 can be manually squeezed or moved closer to the inner guide post 240, allowing a release of the male portion 200 from the female portion 215. In another exemplary embodiment, the outer guide posts 230 can be moved closer to or approach the inner guide post 240 by a trigger assembly, as will be described later on in the disclosure.

FIGS. 3A and 3B show an example embodiment of the current technology comprising a remote release assembly. The remote release assembly can comprise a remote release assembly enclosure 300, at least one cable assembly 311, a trigger assembly 360, and a plurality of attachment assemblies 440, 450. The remote release assembly enclosure can be, but is not limited to, a housing, a box, an enclosure, or a receptacle having any number of sides defining an area within. The remote release assembly enclosure 300 can be made of any material known in the art, including, but not limited to, metals or plastics. The remote release assembly enclosure 300 can be covered or wrapped in a material compatible with the Modular Lightweight Load-carrying Equipment (MOLLE) standard. The remote release assembly enclosure 300 can be attached to a person in any way known in the art, including, but not limited to: Velcro, clips, adhesive, straps, buttons, MOLLE, and ties.

The remote release assembly enclosure 300 can have a connection side 370 and a trigger side 330. Though the trigger side 330 and connection side 370 are shown on opposite ends of the remote release assembly enclosure 300, it should be appreciated that the trigger side 330 and connection side 370 can be located on any side of the remote release assembly enclosure 300, including on the same side. At least one cable assembly 311 can be coupled to the remote release assembly. As depicted in FIGS. 3A and 3B, the at least one cable assembly 311 can traverse through the remote release enclosure 300 from the connection side 370 to the trigger side 330. The at least one cable assembly 311 can be anchored to the connection side 370 of the remote release enclosure 300 using any method known in the art. It should be appreciated that two cable assemblies 311 are shown, but there can be any number of cable assemblies 311 attached to the remote release assembly enclosure 300.

The at least one cable assembly 311 can be a cable assembly as described in the previous examples. The remote release assembly is described with respect to a cable assembly as described above comprising an outer shell 310 and a plurality of inner cables 320. Referring to FIGS. 3A and 3B, the outer shell 310 of the cable assembly 311 can be anchored to the connection side 370 of the remote release enclosure 300. The plurality of inner cables 320 can traverse through the remote release enclosure 300 from the connection side 370 to the trigger side 330. The plurality of inner cables 320 can enter the remote release enclosure 300 at the connection-side aperture (not show) and can pass through the trigger-side aperture 340 to terminate at the trigger side 330. The ends of each of the plurality of inner cables 320 that are proximal to the trigger side 330 of the remote release enclosure 300 can terminate at the trigger assembly 360.

The trigger assembly 360 can include a trigger handle 350. The trigger handle 350 can comprise a ring, wherein at least one of the plurality of inner cables 320 terminates at the curved surface of the ring. FIGS. 3A and 3B illustrate a D-Ring for exemplary purposes, but persons of ordinary skill in the art will appreciate that the trigger handle can be coupled to the plurality of inner cables 320 by other attachments, such as ties, circular rings, clips, or any other types of attachments known in the art. The flat side of the trigger handle 350 can anchor the trigger assembly 360 to the remote release enclosure 300. The trigger assembly 360 can be made of any material known in the art, including, but not limited to a MOLLE-compatible material, nylon webbing, cloth, metal, or plastic. The trigger assembly 360 should be of a size able to be gripped by the user, but can be of any useful length. The trigger assembly 360 can be removably coupled to the at least one cable assembly, such that the trigger 350 can be removed and replaced with a different trigger handle 350 as required or dependent upon user preference. It should be noted that a stopper (not shown) can be attached to both the trigger handle 350 and the connection side 370 to prevent the over-extension of any of the plurality of inner cables 320. The stopper (not shown) can be made of cloth, metal, plastic or any other appropriate material and can be of a length appropriate to prevent the at least one inner wire 320 from extending past a pre-determined point. The stopper can be coupled to the trigger assembly 360 and to the connection side 370 or to the trigger side 330 of the remote release enclosure 300.

The plurality of attachment assemblies (not pictured in FIGS. 3A and 3) can each be coupled to an opposite end of a respective cable assembly 310. The coupling of the attachment assemblies and the respective cable assembly 310 can operatively couple the attachment assembly to the trigger assembly 360. The attachment assemblies can be a side buckle, a side release buckle, and end release buckle, a snap buckle, or any other similar attachment assembly. For example, if an attachment assembly having a male portion and a female portion, such as the attachment assembly described above, is coupled to the trigger assembly 360, the trigger assembly 360 can be actuated to release or disengage or release the male portion from the female portion. For example, when the trigger 350 is activated, the movement of the trigger assembly 360 can be transferred to each of the plurality of attachment assemblies such that at least a portion of the outer guide posts of the male portions approaches the inner guide posts of each of the plurality of attachment assemblies. The coupling of the attachment assembly with its respective cable assembly 310 is described in more detail below.

Figure 4:
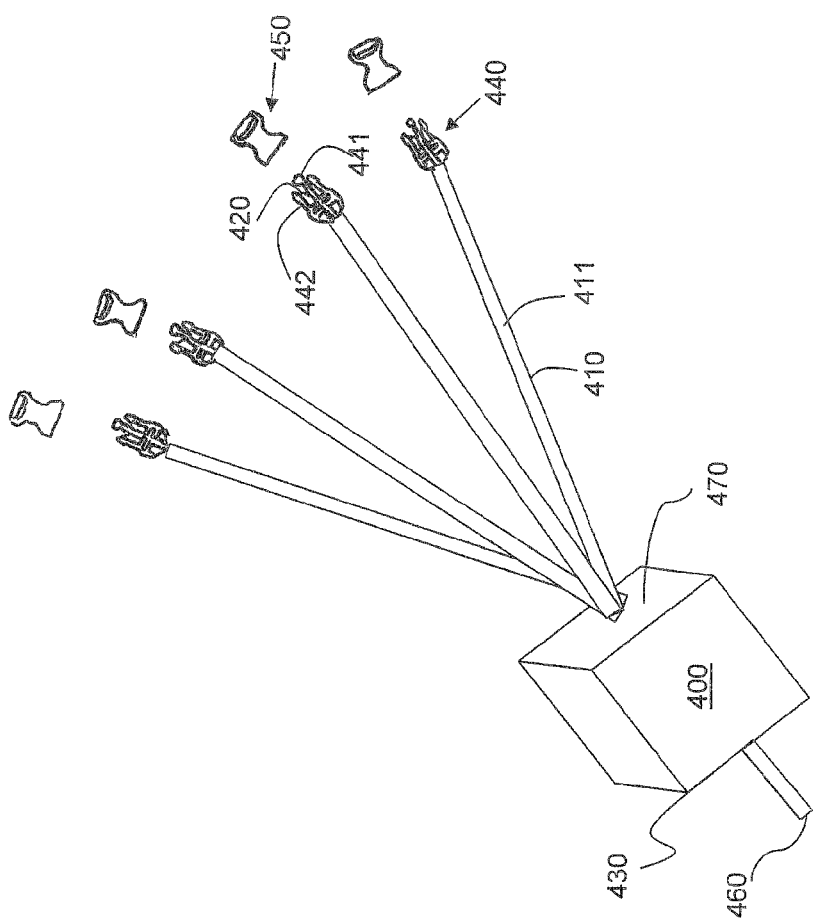
FIG. 4 is a perspective view of a system for quick release in accordance with an exemplary embodiment.

FIG. 4 shows an example embodiment wherein multiple cable assemblies 410 can be activated from a single, remote trigger assembly 400. While four cable assemblies 410 are shown, it should be appreciated that any number of cable assemblies 410 can be activated from a single, remote trigger assembly 400. The multiple cable assemblies 410 can be attached to the connection side 470 of the remote release enclosure 400. The trigger 460 can be located on the trigger side 430 of the remote release enclosure 400. The male portion 440 of the attachment assembly can be secured, fixed, or attached to the female portion 450 of the attachment assembly. Each of the plurality of inner cables 420 of each cable assembly 410 can run from the outer guide posts 442 of the male portion of the corresponding attachment assembly 440, through the inner guide post 441, transversely through the outer shell 411 of the cable assembly 410, through a connection-side aperture (not shown) in the remote trigger assembly 400, through a trigger side aperture (not shown) in the remote trigger assembly 400, and can finally terminate at or affix to the trigger handle (not shown), which is further connected to the trigger assembly 460. Such a coupling permits movement of the trigger assembly 460 to transfer to each of the plurality of attachment assemblies 440, 450, whereby at least a portion of each of the outer guide posts 442 of each of the plurality of attachment assemblies approaches each of the inner guide posts 441 of each of the plurality of attachment assemblies. For example, pulling, tensioning, twisting or activating the trigger 460 of the remote trigger assembly 400 can retract the plurality of inner cables 420 of the cable assemblies 410, which can retract the outer guide posts 441 on the male portions 440 of the attachment assemblies. Consequently, the male portion 440 of the attachment assembly can be disengaged or released from the female portion 450. It should be appreciated that each male portion 440 can be disengaged manually from each respective female portion 450 of an attachment assembly by squeezing or pressing the outer guide posts 442 towards the inner guide post 441.

The remote release assembly described herein can be configured with a backpack, belt, or other utility harness worn by a user. The remote release assembly can be attached to a backpack, belt, or other utility harness by attaching the remote release enclosure 400 via a clip, ties, adhesive, threads, or any other attachment. The user can attach equipment, such as a water bottle, compass, or other types of equipment to a respective female portion 450 of an attachment assembly. The equipment can then be attached or secured to the backpack, belt, or other utility harness by engaging, snapping, or securing the female portion 450 to the corresponding male portion 440 of the attachment assembly. When the user desires to remove or release the equipment from the backpack or belt, the outer guide posts 440 can be manually squeezed or pressed towards the inner guide post of the attachment assembly corresponding to the individual piece of equipment. Alternatively, if the user desires to remove or release all pieces of equipment from the backpack or belt, the trigger assembly 460 can be actuated which transfers movement of the trigger assembly 460 to the plurality of attachment assemblies, whereby at least a portion of each of the outer guide posts 442 of each of the plurality of attachment assemblies approaches each of the inner guide posts 441 of each of the plurality of attachment assemblies. For example, pulling, tensioning, twisting or activating the trigger 460 of the remote trigger assembly 400 can retract the plurality of inner cables 420 of the cable assemblies 410, which can retract the outer guide posts 441 on the male portions 440 of the attachment assemblies. Consequently, the male portion 440 of the attachment assembly can be disengaged or released from the female portion 450, which releases each piece of equipment from the backpack or belt to which the remote release enclosure 400 is attached.

Exemplary embodiments have been described hereinabove regarding the implementation of the remote release assembly on a carrying device, such as a backpack. However, one of ordinary skill in the art will appreciate that this disclosure relates to a system and method for quick release. Various modifications to and departures from the disclosed embodiments will occur to those having skill in the art. The subject matter that is intended to be within the spirit of this disclosure is set forth in the following claims.

What is claimed is:

1. A remote release assembly comprising:
   a remote release enclosure having a connection side and a trigger side;
   at least one cable assembly traversing through the release enclosure from the connection side to the trigger side;
   a trigger assembly coupled to an end of the at least one cable assembly, wherein said end is located proximal to the trigger side of the release enclosure;
   a plurality of attachment assemblies coupled to an opposite end of the at least one cable assembly, wherein each of the plurality of attachment assemblies comprise a male portion and a female portion, said male portion and female portion configured for mating engagement with each other, wherein the at least one cable assembly comprise a plurality of inner cables, and wherein the male portion further comprises an inner guide post between at least two outer guide posts; and
   wherein the trigger assembly is operatively coupled to each of the plurality of attachment assemblies via the at least one cable assembly.

2. The remote release assembly of claim 1, wherein each inner cable is coupled to a single male portion of each of the plurality of attachment assemblies.

3. The remote release assembly of claim 2, wherein each one of the inner cables extends through the inner guide post of each corresponding attachment assembly from a proximate end of the inner guide post towards a distal end of the inner guide post, said each one of the inner cables exiting the inner guide post at the distal end and coupling to at least one of the at least two outer guide posts.

4. The remote release assembly of claim 3, wherein each of the at least one inner cables includes two attachment portions such that one or the attachment portions couples to the outer guide post located to a right side of the inner guide post and a second one of the attachment portions couples to the outer guide post located to a left side of the inner guide post.

5. The remote release assembly of claim 4, wherein movement of the trigger assembly is transferred to each of the plurality of attachment assemblies, whereby at least a portion of the outer guide posts of each of the plurality of attachment assemblies approaches the inner guide post of each of the plurality of attachment assemblies.

6. The remote release assembly of claim 1, wherein the trigger assembly is removably coupled to the at least one cable assembly.

7. The remote release assembly of claim 1, further comprising a ring for coupling the cable assembly to the trigger assembly.

8. The remote release assembly of claim 1, wherein each of the plurality of attachment assemblies is one of a side buckle, a snap buckle, and an end release buckle.

9. The remote release assembly of claim 1, wherein the at least one cable assembly comprises an outer shell.

10. The remote release assembly of claim 9, wherein each of the plurality of inner cables has at least two members.

* * * * *